United States Patent
Wang et al.

(10) Patent No.: US 8,039,492 B2
(45) Date of Patent: Oct. 18, 2011

(54) SUBSTITUTED CYCLIC COMPOUND, ITS PREPARATION PROCESS AND ITS MEDICAL USE

(75) Inventors: Mingwei Wang, Shanghai (CN); Na Li, Shanghai (CN); Xin Xie, Shanghai (CN); Qing Liu, Shanghai (CN); Caihong Zhou, Shanghai (CN); Fajun Nan, Shanghai (CN); Guangxing Wang, Shanghai (CN)

(73) Assignee: Shanghai Institute of Materia Medica, Chinese Academy of Sciences, Shanghai (CN)

(*) Notice: Subject to any disclaimer, the term of this patent is extended or adjusted under 35 U.S.C. 154(b) by 551 days.

(21) Appl. No.: 11/993,440

(22) PCT Filed: Jun. 21, 2006

(86) PCT No.: PCT/CN2006/001410
§ 371 (c)(1), (2), (4) Date: Jun. 16, 2008

(87) PCT Pub. No.: WO2006/136101
PCT Pub. Date: Dec. 28, 2006

(65) Prior Publication Data
US 2010/0168183 A1      Jul. 1, 2010

(30) Foreign Application Priority Data
Jun. 24, 2005   (CN) ................... 2005 1 0027131

(51) Int. Cl.
*A01N 43/40*     (2006.01)
(52) U.S. Cl. ............ 514/342; 548/228; 514/444; 549/59
(58) Field of Classification Search .............. 548/228; 514/342, 444; 549/59
See application file for complete search history.

(56) References Cited

FOREIGN PATENT DOCUMENTS
CN    1626521 A    6/2005

OTHER PUBLICATIONS

Marino, Understanding Insulin Resistance Key to Diabetes Prevention.*

(Continued)

*Primary Examiner* — Brandon Fetterolf
*Assistant Examiner* — Jean Cornet
(74) *Attorney, Agent, or Firm* — Baker & Hostetler LLP

(57) ABSTRACT

The present invention provides a substituted cyclic compound of the following general formula I or II:

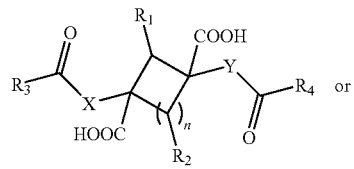

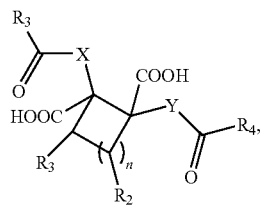

its preparation process and its use as a glucagon-like peptide-1 receptor regulator for preventing or treating metabolic disorders including, but not limited to, diabetes, insulin resistance and obesity, etc.

8 Claims, 3 Drawing Sheets

OTHER PUBLICATIONS

Wolff, Manfred E., Ed. Burgers Medicinal Chemistry and Drug Discovery—Fifth Edition, New York: John Wiley & Sons,1996, vol. 1, pp. 975-976).*
Vippagunta et al. ("Crystalline solids"; 2001; Advanced Drug Delivery Reviews; 48: 3-26).*
Schafer et al. Drug Discovery Today 2008, 13 (21/22), 913-916.*
Horig et al. Journal of Translational Medicine 2004, 2(44).*
Baggio et al "Chronic exposure to GLP-1R agonists promotes homologous GLP-1 receptor desensitization in vitro but does not attenuate GLP-1R-dependent glucose homeostasis in vivo", Diabetes supplement 3, vol. 53, Dec. 2004.*

Tetsuyuki Iwamoto and Setsuo Kashino, "Topochemical Studies. XVI. Direct Observation of the Solid-State Photoreaction of a-(Acetylamino) cinnamic Acid Dihydrate by Single Crystal X-Ray Diffraction," Department of Chemistry, Faculty of Science, Okayama University, Tsushima, Okayama 700 (Feb. 24, 1993).

* cited by examiner

SUBSTITUTED CYCLIC COMPOUND, ITS PREPARATION PROCESS AND ITS MEDICAL USE

CROSS-REFERENCE TO RELATED APPLICATIONS

This application is the National Stage of International Application No. PCT/CN2006/001410 filed Jun. 21, 2006, which claims the benefit of Chinese Application No. CN200510027131.X filed Jun. 24, 2005, the entire disclosures of which are incorporated herein by reference.

TECHNICAL FIELD

The present invention provides a substituted cyclic compound, its preparation process and its medical use as glucagon-like peptide-1 receptor (GLP-1R) regulator in preventing or treating metabolic disorders (including, but not limited to, diabetes mellitus, insulin resistance and obesity, etc.).

BACKGROUND ART

Diabetes mellitus is a clinical syndrome caused by the interaction of various factors including genetic traits and environmental contributors. Diabetes is primarily divided into type I and type II. Wherein, the basic pathophysiologic mechanism of type I diabetes mellitus relates to absolute hyposecretion of insulin, which is treated clinically mainly by supplementing insulin and thus is also named as insulin dependent diabetes mellitus. Over 95% of the patients are suffering from type II diabetes mellitus. In the clinical research, it is found that most of the patients suffering from type II diabetes mellitus can synthesize normal or even excessive insulin, but since the sensitivity of target cell to insulin is decreased (which is also named as "insulin resistance"), which causes the relative insufficiency of insulin, it is also named as non-insulin dependent diabetes mellitus. Insulin resistance is a key factor during the occurrence and development of type II diabetes mellitus.

Since the pathogenesis for the above two types of diabetes mellitus are different, the drugs for treating them are far different. At present, the drugs for treating type I diabetes mellitus mainly include exogenous insulin (including genetically recombinant human insulin and animal insulin), drugs having insulin-like effect, insulin-like growth factor-1 and Jin Qi hypoglycemic tablet, etc. The drugs for treating type II diabetes mellitus include sulphonylureas, biguanides, other insulin sensitizers and auxiliary means, etc.

After the sulphonylurea hypoglycemic drugs bind to the receptors of pancreatic islet β-cell membrane, the potassium ion channels are closed, thereby blocking flowout of potassium ion and inducing depolarization of the cell membrane, so that the $Ca^{2+}$ channels are opened to allow the extracellular calcium ions to flow inward. The increase in the concentration of intracellular calcium ions triggers the release of insulin. Sulphonylurea hypoglycemic drugs can be divided into two generations according to their time of coming into existence. The first generation includes tolpropamide, and the second generation includes glibenclamide (diabeta), gliclazide (diamicron), glipizide (minidiab) and gliquidone, etc.

Biguanide hypoglycemic drugs can inhibit appetite, improve the binding of insulin to the receptors, promote the anaerobic glycolysis of glucose in cells, inhibit tissue respiration and inhibit hepatic gluconeogenesis. The biguanide hypoglycemic drugs mainly include metformin, phenformin and buformin.

Other hypoglycemic drugs mainly include thiazolidinedione drugs (such as troglitazone, rosiglitazone, and pioglitazone, etc.), β3-adrenoceptor regulators, glucagon receptor antagonists, fatty acid metabolism interfering agents, α-glycosidase inhibitors (such as acarbose, voglibose, miglitol, etc.), and aldose reductase inhibitors and the like.

The deep research on glycometabolism-related endogenous peptide hormone provides a new idea for the treatment of diabetes mellitus. When human body intakes nutrient materials, the enteroendocrine cells release enteropeptide hormone, mainly including glucagon-like peptide-1 (GLP-1) and glucose-dependent insulinotropic peptide (GIP), which regulates the metabolism of organism by affecting the insulin generation, gastrointestinal peristalsis, pancreatic islet cell proliferation, etc. Wherein, GLP-1 is secreted by the enteric Langerhans cells, and activates adenylate cyclase to improve the cAMP level by specifically binding to the GLP-1 receptor of pancreatic islet β-cells, so as to further activate the protein kinase. The metabolic signal (glycometabolism) and kinase signal (binding to GLP-1) cooperate at the cell membrane level to finally cause the $Ca^{2+}$ channel to open and $Ca^{2+}$ to flow inward, thereby further stimulating the secretion of insulin while inhibiting the generation of glucagon, so that the postprandial blood sugar concentration is decreased and maintained at a constant level. Also, GLP-1 has the function of neuroregulation, and can retard gastric emptying and inhibit appetite. Normally, the effect of GLP-1 for stimulating insulin secretion depends on the blood sugar concentration. As the blood glucose concentration lowers, the effect of GLP-1 for stimulating insulin secretion accordingly decreases, namely self-limited hypoglycemic effect, and thus hypoglycemia will not occur. The drugs with the GLP-1-like action are greatly desirable for the treatment of diabetes mellitus.

GLP-1, which is directly injected to the patients with diabetes for continued 6 weeks, may effectively control the levels of blood sugar and free fatty acids, and improve the function of β-cells. Since the half life of GLP-1 in body is less than 5 minutes, its clinical application is greatly limited. A GLP-1 analog that binds to albumin, as developed by Novo Nordisk Co., Danmark (Trade Name "Liraglutide"), may have a half life of up to 10 hours. The result of Clinical Trial Phase I showed that the drug can obviously improve the symptoms of diabetes mellitus while having no notable virulent side-effect. It can be predicted that Clinical Trial Phase III will be carried out before long. Exendin-4 (also named as AC2993, with the trade name of Exenatide) is a GLP-1 analog (a polypeptide composed of 39 amino acids) developed by the Amylin Medical Co., USA, which was originally isolated from the saliva of an American venomous lizard. In the clinical trials, it is found that, for normal volunteers, Exendin-4 can retard gastric emptying, inhibit appetite and stimulate insulin secretion; for the patients with diabetes of type II, Exendin-4 may stimulate insulin secretion, and obviously decrease the postprandial concentrations of blood sugar and glucagon, and can reduce the body weight of the patients after a long-time use. The side effects resulted therefrom mainly include temporary headache, nausea and vomit. Exendin-4 had been authorized by the American FDA to be marketed as the drugs for treating diabetes of type II at the end of April in 2005. Owing to the use of the Medisorb controlled release technology of Alkerme Co., the controlled release preparation based on Exendin-4, AC2993LAR, as developed by Amylin Co., only needs to be injected once a month, which is being in the Clinical Trial Phase II. Basing on the effect of GLP-1R agonists for promoting the growth and proliferation of pancreatic islet β-cell, American NIH has started the Clinical Trial Phase I of using Exendin-4 (AC2993) to treat type I diabetes mellitus. Since the polypeptide drugs are inconvenient for oral administration, the various international pharmaceutical organizations focus on searching for non-peptide GLP-1R regulators and developing new types of drugs treating diabetes mellitus that have independent intellectual property. However, there are no reports about non-peptide GLP-1R regulators now, except for GLP-1 and analogs thereof.

CONTENTS OF THE INVENTION

The object of the present invention is to provide a compound of the following general formula I or II and its pharmaceutically acceptable salts.

Another object of the present invention is to provide a process for preparing a compound of the following general formula I or II.

Yet another object of the present invention is to provide a pharmaceutical composition comprising the compound of the following general formula I or II.

Still another object of the present invention is to provide the medical application of the compound of the following general formula I or II as the glucagon-like peptide-1 receptor regulator in preventing or treating metabolic disorders (including, but not limited to, diabetes, insulin resistance and obesity, etc.).

The invention provides the glucagon-like peptide-1 receptor regulators, thereby adding members to the group of drugs for preventing and treating diabetes. The invention relates to the compound of the following general formula I or II, and pharmaceutically acceptable salts thereof and all stereoisomers and optical isomers thereof, or prodrugs having same pharmacological effect therewith, esters, solvates or metal complexes thereof

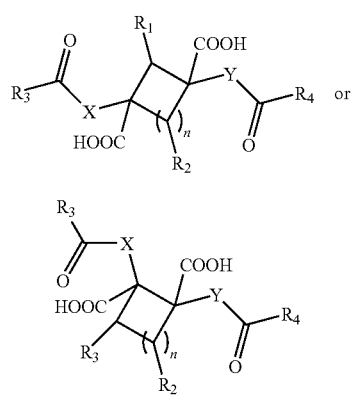

wherein, n is any number within the range of 0 to 3, X and Y independently are O, S or N;

wherein, $R_1$ and $R_2$ independently are one of the substituents selected from the group consisting of: hydrogen, halogen, alkane, cycloalkane, hydroxyl, nitro, carboxyl, aldehyde, alkoxy, amino, alkylamino, amido, carbamide, mercapto, alkylthio, ether, thioether, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio;

$R_3$ and $R_4$ independently are one of the substituents selected from the group consisting of: hydrogen, alkane, cycloalkane, alkoxy, amino, alkylamino, amido, carbamide, alkylthio, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio.

Preferably, the compound of the formula I and II is characterized in that: When n is 0, wherein $R_1$ is one of the substituents selected from the group consisting of: hydrogen, halogen, alkane, cycloalkane, hydroxyl, nitro, carboxyl, aldehyde, alkoxy, amino, alkylamino, amido, carbamide, mercapto, alkylthio, ether, thioether, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $R_3$ and $R_4$ independently are one of the substituents selected from the group consisting of: hydrogen, alkane, cycloalkane, alkoxy, amino, alkylamino, amido, carbamide, alkylthio, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; X and Y independently are O, S or N.

More preferably, when n is 1-3, wherein $R_1$ and $R_2$ independently are one of the substituents selected from the group consisting of: hydrogen, halogen, alkane, cycloalkane, hydroxyl, nitro, carboxyl, aldehyde, alkoxy, amino, alkylamino, amido, carbamide, mercapto, alkylthio, ether, thioether, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $R_3$ and $R_4$ independently are one of the substituents selected from the group consisting of: hydrogen, alkane, cycloalkane, alkoxy, amino, alkylamino, amido, carbamide, alkylthio, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio.

X and Y independently are O, S or N.

More preferably, the compound of above formula I and II is cyclic compound, being characterized in that: when n is 0; X and Y independently are O, S or N; $R_1$ is

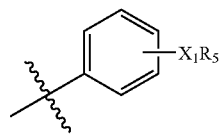

wherein, $R_5$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH;

$R_3$ and $R_4$ independently are

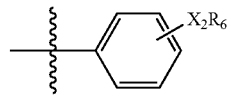

wherein, $R_6$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; or, $R_3$ and $R_4$ independently are

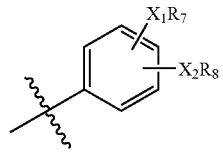

wherein, $R_7$ and $R_8$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cycloalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkenoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH; or, $R_3$ and $R_4$ independently are

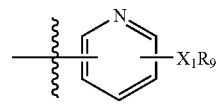

wherein, $R_9$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; or, $R_3$ and $R_4$ independently are

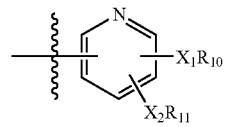

wherein, $R_{10}$ and $R_{11}$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; when $X_1$ is O, S or NH; $X_2$ is O, S or NH; when $R_1$ is

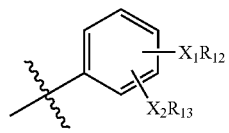

wherein, $R_{12}$ and $R_{13}$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH;

$R_3$ and $R_4$ independently are wherein, $R_6$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_2$ is O, S or NH;

or, $R_3$ and $R_4$ independently are wherein, $R_7$ and $R_8$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH;

or, $R_3$ and $R_4$ independently are wherein, $R_9$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH;

or, $R_3$ and $R_4$ independently are

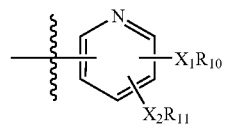

wherein, $R_{10}$ and $R_{11}$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cycloalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH.

Furthermore preferably, when $R_1$ is

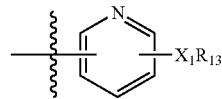

wherein, $R_{13}$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; when $X_1$ is O, S or NH;

$R_3$ and $R_4$ independently are

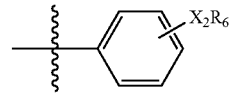

wherein, $R_6$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_2$ is O, S or NH;
or, $R_3$ and $R_4$ independently are

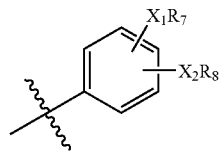

wherein, $R_7$ and $R_8$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cycloalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH;
or, $R_3$ and $R_4$ independently are

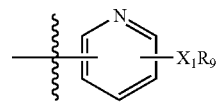

wherein, $R_9$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH;
or, $R_3$ and $R_4$ independently are

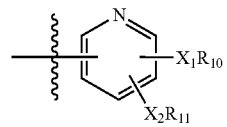

wherein, $R_{10}$ and $R_{11}$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cycloalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH.
When $R_1$ is

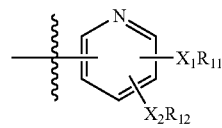

wherein, $R_{11}$ and $R_{12}$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cycloalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH; $R_3$ and $R_4$ independently are

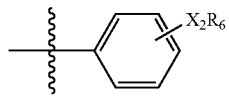

wherein, $R_6$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_2$ is O, S or NH;

or, $R_3$ and $R_4$ independently are

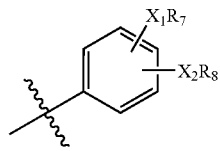

wherein, $R_7$ and $R_8$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH;

or, $R_3$ and $R_4$ independently are

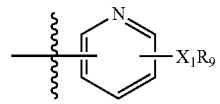

wherein, $R_9$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH;

or, $R_3$ and $R_4$ independently are

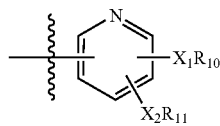

wherein, $R_{10}$ and $R_{11}$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH.

Furthermore preferably, when n is any number within the range of 1-3; X and Y independently are O, S or N; $R_1$ and $R_2$ independently are

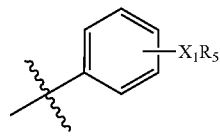

wherein, $R_5$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_2$ is O, S or NH;

$R_3$ and $R_4$ independently are

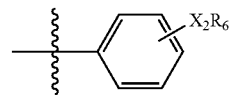

wherein, $R_6$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_2$ is O, S or NH;

or, $R_3$ and $R_4$ independently are

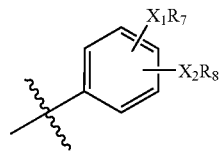

wherein, $R_7$ and $R_8$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cycloalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH;
or, $R_3$ and $R_4$ independently are

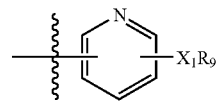

wherein, $R_9$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH;
or, $R_3$ and $R_4$ independently are

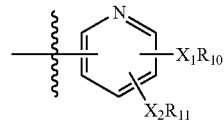

wherein, $R_{10}$ and $R_{11}$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH.
When $R_1$ and $R_2$ independently are

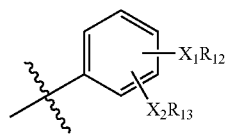

wherein, $R_{12}$ and $R_{13}$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH;
$R_3$ and $R_4$ independently are wherein, $R_6$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_2$ is O, S or NH;
or, $R_3$ and $R_4$ independently are wherein, $R_7$ and $R_8$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH;
or, $R_3$ and $R_4$ independently are wherein, $R_9$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio; ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH;

or, $R_3$ and $R_4$ independently are

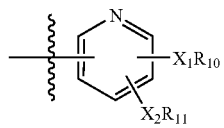

wherein, $R_{10}$ and $R_{11}$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cycloalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH.

Furthermore preferably, when $R_1$ and $R_2$ independently are

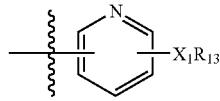

wherein, $R_{13}$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; when $X_1$ is O, S or NH; $R_3$ and $R_4$ independently are

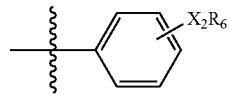

wherein, $R_6$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_2$ is O, S or NH;

or, $R_3$ and $R_4$ independently are

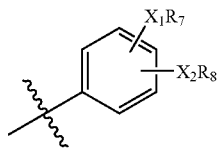

wherein, $R_7$ and $R_8$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH;

or, $R_3$ and $R_4$ independently are

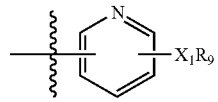

wherein, $R_9$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH;

or, $R_3$ and $R_4$ independently are

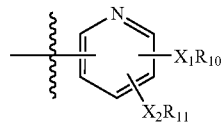

wherein, $R_{10}$ and $R_{11}$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH.

When $R_1$ and $R_2$ independently are

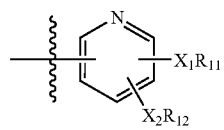

wherein, $R_{11}$ and $R_{12}$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; when $X_1$ is O, S or NH; $X_2$ is O, S or NH; $R_3$ and $R_4$ independently are

[structure with $X_2R_6$ substituent on phenyl ring]

wherein, $R_6$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkenoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_2$ is O, S or NH;

or, $R_3$ and $R_4$ independently are

[structure with $X_1R_7$ and $X_2R_8$ substituents on phenyl ring]

wherein, $R_7$ and $R_8$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH;

or, $R_3$ and $R_4$ independently are

[structure with pyridyl ring bearing $X_1R_9$ substituent]

wherein, $R_9$ is one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cylcoalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; or, $R_3$ and $R_4$ independently are

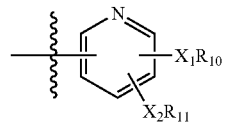

wherein, $R_{10}$ and $R_{11}$ independently are one of the substituents selected from the group consisting of: H; $C_1$-$C_6$ alkyl; $C_1$-$C_6$ alkyl substituted with one, two or three groups selected from halogen, $C_1$-$C_6$ alkoxy, or hydroxyl; $C_2$-$C_6$ alkenyl; $C_2$-$C_6$ alkynyl; $C_3$-$C_6$ cycloalkyl; $C_3$-$C_6$ cycloalkyl substituted with one, two or three groups selected from halogen, $C_1$-$C_6$ alkoxy, or hydroxyl; aryl; benzyl; furyl; pyranyl; thienyl; pyrrolyl; 2-, 3- or 4-pyridyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio; $C_1$-$C_6$ alkanoyl substituted with one, two or three groups selected from halogen, $C_1$-$C_6$ alkoxy, or hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, or hydroxyl; adamantine formyl; substituted adamantine formyl; aroyl; benzoyl; furoyl; pyranoyl; thenoyl; pyrroyl; $X_1$ is O, S or NH; $X_2$ is O, S or NH.

In addition, preferably, the compound or its pharmaceutically acceptable salts is supplied, in the form of pharmaceutical composition, either alone or in combination with pharmaceutically acceptable carriers or excipients. The present invention also provides the drug comprising the above compound, useful for preventing or treating metabolic disorders (including, but not limited to, diabetes, insulin resistance and obesity, etc).

On the other hand, the invention relates to the method of preventing or treating metabolic disorders, including, but not limited to, diabetes, insulin resistance and obesity, etc. The method comprises administering to a subject, who needs or would like to accept treatment or prevention, an effective dose of a compound that selectively regulates the glucagon-like peptide-1 receptor, or pharmaceutically acceptable salts thereof to thereby treat or prevent the diseases or symptoms. Preferably, the above metabolic disorders are prevented or treated by administering an effective dose of a compound of the following general formula I or II, or pharmaceutically acceptable salts thereof and all stereoisomers and optical isomers thereof, or prodrugs having same pharmacological effect therewith, esters, solvates or metal complexes thereof,

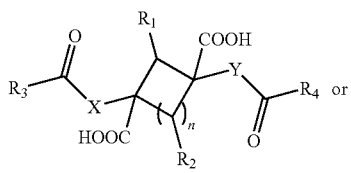

I

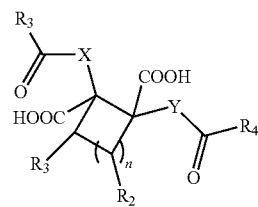

II wherein, n is any number within the range of 0 to 3. X and Y independently are O, S or N;

wherein, $R_1$ and $R_2$ independently are one of the substituents selected from the group consisting of: hydrogen, halogen, alkane, cycloalkane, hydroxyl, nitro, carboxyl, aldehyde, alkoxy, amino, alkylamino, amido, carbamide, mercapto, alkylthio, ether, thioether, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio;

$R_3$ and $R_4$ independently are one of the substituents selected from the group consisting of: hydrogen, alkane, cycloalkane, alkoxy, amino, alkylamino, amido, carbamide, alkylthio, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio.

On the other hand, the present invention relates to a combined preparation, which comprises, present either alone or in combination with the pharmaceutically acceptable carriers or excipients, a compound capable of selectively regulating glucagon-like peptide-1 receptor, especially activating the function of the receptor, or pharmaceutically acceptable salts thereof and all stereoisomers and optical isomers thereof, or prodrugs having same pharmacological effect therewith, esters, solvates or metal complexes thereof. The compound is characterized by the following formula I or II:

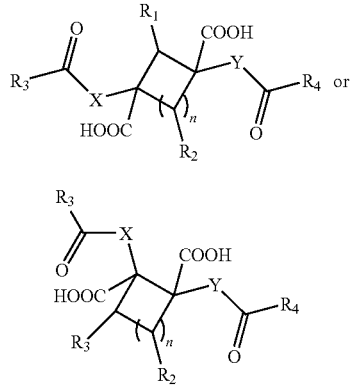

wherein, n is any number within the range of 0 to 3, X and Y independently are O, S or N;

wherein, $R_1$ and $R_2$ independently are one of the substituents selected from the group consisting of: hydrogen, halogen, alkane, cycloalkane, hydroxyl, nitro, carboxyl, aldehyde, alkoxy, amino, alkylamino, amido, carbamide, mercapto, alkylthio, ether, thioether, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio;

$R_3$ and $R_4$ independently are one of the substituents selected from the group consisting of: hydrogen, alkane, cycloalkane, alkoxy, amino, alkylamino, amido, carbamide, alkylthio, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio.

The present invention provides a kit containing the above combined preparation. The invention further provides the application of the above combined preparation for preventing or treating metabolic disorders (including, but not limited to, diabetes, insulin resistance and obesity, etc.), thereby achieving the therapeutic effect of selectively activating the glucagon-like peptide-1 receptor, and improving the symptom and the quality of life of the patients with diabetes.

In order to clarify the content of the invention, which does not limit the invention, the present invention is detailedly described in the following parts.

A. Definitions

Unless otherwise defined, the technical and scientific terms used herein have the meanings commonly understood by one skilled in the art. All of the patents, applications, published applications and other publications and sequences, which are derived from gene bank and other databases, are incorporated herein in their entireties by reference. When there is any conflict or difference between the definitions in this part and those as involved or cited in any of the patents, applications, published applications, and other publications and sequences, which are derived from gene bank and other databases, the definitions in this part are valid.

The term "a" or "one" as used herein refers to "at least one" or "one or more".

The term "metabolic disorders" as used herein refers to the relevant symptoms and/or diseases as a result of metabolic disturbance of saccharide, fat or protein, etc. caused by various factors.

The term "diabetes" used herein refers to a poly-pathogenic metabolic disease, which is featured with chronic hyperglycemia accompanied by metabolic disturbance of saccharide, fat or protein caused by insulin secretion and/or function defect. With prolonging of time of suffering from diabetes, if the metabolic disorders in body cannot be well controlled, it will lead to chronic complications of the tissues/organs such as eyes, kidney, nerve, blood vessel and heart, so as to finally cause blindness, gangrene of lower limb, uraemia, cerebral apoplexy or myocardial infarction, and even be dangerous to life.

The term "insulin resistance" as used herein refers to that the sensitivity of peripheral tissues in human body to insulin is decreased, and the target tissues such as muscle and fat resist the effect of insulin promoting the intake of glucose. Insulin resistance widely exists in the type II diabetes mellitus, almost occupying for more than 90%, which is one of the main factors causing the type II diabetes mellitus.

The term "obesity" as used herein refers to the phenomenon that the quantity of fat in human body is superfluous, the body weight of man being over 25% more than the standard weight or the body weight of woman being over 30% more than the standard weight. The factors causing obesity include heredity, hypothalamic disorder, endocrine disturbance, hyperphagia and shortage of exercise.

The "effective dose" of a compound for treating a specific disease refers to a dose that is sufficient to improve or relieve the symptoms accompanied with the disease to some degree. The dose may be administered as a single dosage, also administered according to the scheme of treatment. The dose may cure the disease, but it is typically administered to improve the symptoms. It may be needed to repetitively administer the drug for improving the symptoms.

The term "pharmaceutically acceptable salts, esters or other derivatives" as used herein includes any salts, esters or other derivatives that are easily prepared via a known method by one skilled in the art. The compounds as thus derived or prepared may be administered as drugs to animal and human being, without any virulent effect. The compounds either have drug activity or are prodrugs.

The term "treatment" as used herein refers to that the diseases and symptoms are improved in any way or have other helpful changes. The treatment also includes the pharmaceutical applications of the compounds of the present invention.

The "improving" of the symptoms of a specific disease by administrating a specific pharmaceutical composition refers to that any allevations, whatever perpetual, temporary, chronic or brief, can be attributed to, or relevant with, the application of the pharmaceutical composition.

The term "substantially pure" as used herein refers to sufficiently uniform so that a person skilled in the art cannot detect any impurity using a standard analytical method, which is used to appraise purity. Said standard analytical method includes, e.g., thin-layer chromatography (TLC), gel electrophoresis and high performance liquid chromatography (HPLC). Or, sufficiently pure also refers to that, even if further purified, the detectable physical-chemical properties, e.g., enzyme activity and biological activity, of the substance will not changed. The methods for purifying a compound to make it substantially chemically pure are well known to those skilled in the art. However, substantially chemically pure compound may be a mixture of stereoisomers or isomers. In this case, further purification may increase the specific activity of the compound.

The term "prodrug" as used herein refers to a compound that is administered in vivo, which can be metabolized or converted into an active form in terms of biology, pharmacology or therapeutics. In order to prepare a prodrug, a pharmaceutically active compound will be modified so that the active compound may be reproduced through a process of metabolism. The prodrug may be designed as a precursor having the changed metabolic stability or transportation property, so as to mask the side effect or toxicity of the drug, and improve the taste of the drug or change its other properties. Once a pharmaceutically active compound is known, those skilled in the art may scheme out the prodrugs of the compound based on the knowledge of pharmacokinetics and drug metabolism in vivo. [See *Medicinal Chemistry A Biochemical Approach*, Oxford University Press, New York, 1985, pages 388-392].

The term "substantially" identical or uniform or similar as used herein means, which may be somewhat changed in the context according to the comprehension about the relevant techniques by those skilled in the art, generally at least 70%, preferably at least 80%, more preferably at least 90%, and most preferably at least 95% identical.

The term "composition" as used herein refers to any mixture, which may be solution, suspension, liquid, powder, ointment, aqueous, non-aqueous or any mixture thereof.

The term "combination" as used herein refers to any combination of two or more.

The term "subject" as used herein includes human and animals, such as dog, cat, cattle, pig, rodent, etc. The experienced executants shall comprehend the subject as those that is suitable and would like to accept the prevention and treatment of diabetes and its complications.

Unless otherwise indicated, any abbreviations of protecting groups, amino acids and other compounds as used herein are the same with their universal, acknowledged abbreviations or their biochemical names as published by IUPAC-IUB Committee.

B. Glucagon-like Peptide-1 Receptor Regulator

The present invention provides glucagon-like peptide-1 receptor regulator, thereby adding members to the group of drugs for preventing and treating diabetes. The invention relates to a compound of the following general formula I or II or pharmaceutically acceptable salts thereof, and all stereoisomers and optical isomers thereof, or prodrugs having same pharmacological effect therewith, esters, solvates or metal complexes thereof,

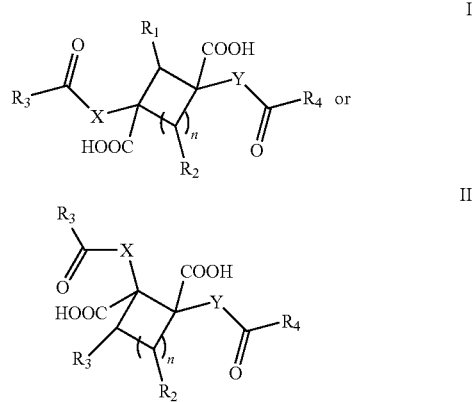

wherein, n is any number within the range of 0-3, X and Y independently are O, S or N;

wherein, $R_1$ and $R_2$ independently are one of the substituents selected from the group consisting of: hydrogen, halogen, alkane, cycloalkane, hydroxyl, nitro, carboxyl, aldehyde, alkoxy, amino, alkylamino, amido, carbamide, mercapto, alkylthio, ether, thioether, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio;

$R_3$ and $R_4$ independently are one of the substituents selected from the group consisting of: hydrogen, alkane, cycloalkane, alkoxy, amino, alkylamino, amido, carbamide, alkylthio, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio.

The compound of the present invention may be a specific stereoisomer, such as R-isomer or S-isomer or mixture thereof, for example, racemic mixture. Compounds considered herein include all kinds of compounds having pharmaceutical activity, or solutions or mixtures thereof. Also included are the hydrated form, such as aqueous solutions, hydrolysates or ionized products of the compounds. Moreover, these compounds may have different amount of water molecules.

The compound of the present invention may be prepared or synthesized according to any suitable methods. Preferably, the compound is prepared according to the synthetic method as cited in the next part F.

In addition, preferably, the compound or pharmaceutically acceptable salts thereof is supplied, in the form of pharmaceutical composition, either alone or in combination with pharmaceutically acceptable carriers or excipients.

The compound of the present invention may be prepared in the form of its pharmaceutically acceptable salts by using any suitable acids. For example, inorganic acids, such as hydrochloric acid, hydrobromic acid, nitric acid, sulfuric acid, phosphoric acid and so on; organic acids, such as formic acid, acetic acid, propionic acid, benzoic acid, maleic acid, fumaric acid, succinic acid, tartaric acid, citric acid and so on; alkyl sulfonic acids, such as methanesulfonic acid, ethanesulfonic acid and so on; and aryl sulfonic acids, such as benzenesulfonic acid, p-toluene sulfonic acid, etc. may be used.

C. Method for Prevention and Treatment

The present invention relates to the method of preventing or treating metabolic disorders (including, but not limited to, diabetes, insulin resistance and obesity, etc.). The method comprises administering to a subject, who needs or would like to accept treatment or prevention, an effective dose of a compound that selectively agitates the glucagon-like peptide-1 receptor, or pharmaceutically acceptable salts thereof to thereby treat or prevent the diseases or symptoms.

Preferably, the above metabolic disorders are prevented or treated by administering an effective dose of a compound of the following general formula I or II or its pharmaceutically acceptable salts and all stereoisomers and optical isomers thereof, or prodrugs having same pharmacological effect therewith, esters, solvates or metal complexes thereof,

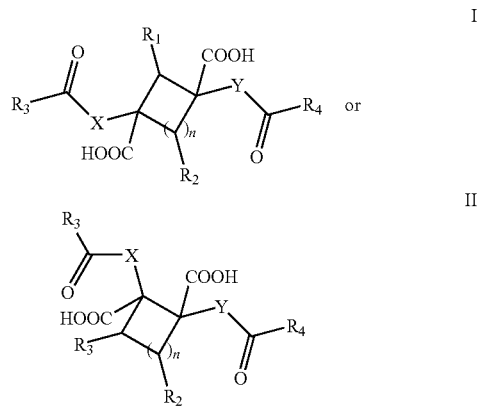

wherein, n is any number within the range of 0-3, X and Y independently are O, S or N;

wherein, $R_1$ and $R_2$ independently are one of the substituents selected from the group consisting of: hydrogen, halogen, alkane, cycloalkane, hydroxyl, nitro, carboxyl, aldehyde, alkoxy, amino, alkylamino, amido, carbamide, mercapto, alkylthio, ether, thioether, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio;

$R_3$ and $R_4$ independently are one of the substituents selected from the group consisting of: hydrogen, alkane, cycloalkane, alkoxy, amino, alkylamino, amido, carbamide, alkylthio, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio.

The method may be used to preventing and treating in any subject, preferably mammals, more preferably human.

The method can be used to prevent any diseases or symptoms caused or accompanied by insulin secretion and/or function disturbance. The preferred diseases or symptoms include diabetes, insulin resistance and obesity, etc.

When preventing or treating the above diseases and symptoms, the compound of the invention may be used alone or in combination with other drugs for treating diabetes including insulin sensitizers that have been marketed or will be marketed. Any suitable drugs for treating diabetes may be used in combination with the compound of the present invention. Wherein, the typical insulin sensitizers include rosiglitazone and pioglitazone, etc.

In one preferred embodiment of the invention, the compound of the invention is used without involving the above insulin sensitizers. More preferably, the compound of the invention is useful for treating or preventing the diseases or symptoms resulted from drug resistance or virulent side-effect produced by administering the drugs for treating diabetes (including insulin sensitizers) that have been marketed or will be marketed.

The compound of the invention may be administered either alone or in combination with other suitable drugs for treating diabetes including insulin sensitizers via any suitable ways. For example, the compound of the invention or pharmaceutically acceptable salts thereof may be administered by the route of intracavitray injection, subcutaneous injection, intravenous injection, intramuscular injection, or intradermic injection, oral or topical application.

Further, in one specific embodiment of the invention, the method further comprises diagnosing and prognostically evaluating the diseases or symptoms of the subject to which the drug is administrated. Any suitable methods may be used for the diagnosis and estimation of the relevant diseases or symptoms and the prognosis. Diagnosis and prognosis may be based on detecting and/or identifying any or all the substances in body, such as glycosylated hemoglobin, enzyme, antigen, antibody, nucleic acid or other pathologic and clinical markers, and the relative symptoms. For example, the diagnostic or prognostic methods disclosed in International Patent WO 01/44815 and U.S. Pat. No. 5,571,674 may be used.

D. Combined Preparation, Kit and Method of Drug Combination

On the other hand, the present invention also relates to a combined preparation, which comprises a compound that selectively regulates the function of glucagon-like peptide-1 receptor, or its pharmaceutically acceptable salts, and one or more drugs for treating diabetes including insulin sensitizers.

Preferably, the combined preparation comprises the compound of the following general formula I or II of the invention or pharmaceutically acceptable salts thereof and all stereoisomers and optical isomers thereof, or prodrugs having same pharmacological effect therewith, esters, solvates or metal complexes thereof, and one or more drugs for treating diabetes including insulin sensitizers,

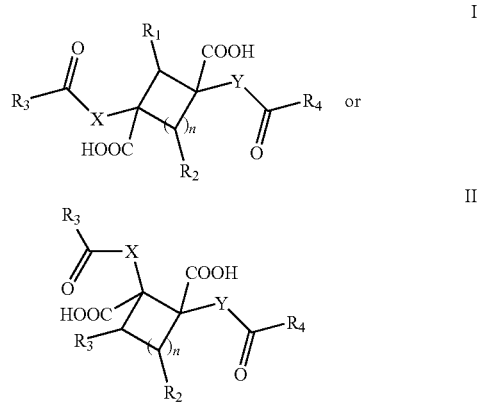

wherein, n is any number within the range of 0-3, X and Y independently are O, S or N;

wherein, $R_1$ and $R_2$ independently are one of the substituents selected from the group consisting of: hydrogen, halogen, alkane, cycloalkane, hydroxyl, nitro, carboxyl, aldehyde, alkoxy, amino, alkylamino, amido, carbamide, mercapto, alkylthio, ether, thioether, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio;

$R_3$ and $R_4$ independently are one of the substituents selected from the group consisting of: hydrogen, alkane, cycloalkane, alkoxy, amino, alkylamino, amido, carbamide, alkylthio, aryl, 2-, 3- or 4-pyridyl, furyl, pyranyl, thienyl, pyrrolyl; aryl substituted with one, two or three groups selected from $C_1$-$C_4$ alkyl, nitro, carboxyl, aldehyde, alkoxy, amino, amido, carbamide, mercapto, methylthio, ethylthio; 2-, 3- or 4-pyridyl substituted with one, two or three groups selected from $C_1$-$C_4$ alkyl, nitro, carboxyl, aldehyde, alkoxy, amino, amido, carbamide, mercapto, methylthio, ethylthio; furyl substituted with one, two or three groups selected from $C_1$-$C_4$ alkyl, nitro, carboxyl, aldehyde, alkoxy, amino, amido, carbamide, mercapto, methylthio, ethylthio; pyranyl substituted with one, two or three groups selected from $C_1$-$C_4$ alkyl, nitro, carboxyl, aldehyde, alkoxy, amino, amido, carbamide, mercapto, methylthio, ethylthio; thienyl substituted with one, two or three groups selected from $C_1$-$C_4$ alkyl, nitro, carboxyl, aldehyde, alkoxy, amino, amido, carbamide, mercapto, methylthio, ethylthio; pyrrolyl substituted with one, two or three groups selected from $C_1$-$C_4$ alkyl, nitro, carboxyl, aldehyde, alkoxy, amino, amido, carbamide, mercapto, methylthio, ethylthio.

In the combined formulation of the invention, any suitable drugs for treating diabetes including insulin sensitizers may be used. In one specific embodiment, the drugs used in the combined formulation may comprise one of more the above drugs for treating diabetes including insulin sensitizers.

In another specific embodiment, a method for preventing and/or treating the diseases or symptoms caused or accompanied by insulin secretion and/or function disturbance is provided, which comprises administering to a subject who needs or would like to accept treatment or prevention an effective dose of the above combined preparation, or pharmaceutically acceptable salts thereof, to thereby treat or prevent said diseases or symptoms.

In yet another specific embodiment, a kit is provided, which comprises the compound of the invention or pharmaceutically acceptable salts thereof, and the specification about the application of said compound or pharmaceutically acceptable salts thereof to treat or prevent the diseases or symptoms caused or accompanied by insulin secretion and/or function disturbance.

In still another embodiment, a kit is provided, which comprises the above combined formulation, and the specification about the application of said combined formulation to treat or prevent diseases or symptoms caused or accompanied by insulin secretion and/or function disturbance.

E. Formulation and Dosage

According to the invention, the compound of the invention, alone or in combination with other drugs, carriers or excipients, is made into preparations for any suitable administration routes, such as intracavitary injection, subcutaneous injection, intravenous injection, intramuscular injection, intradermic injection, oral or local application. The method herein includes delivering a drug preparation by injection, which is administrated in the form of single-dose in ampoule or multi-dose vessel together with added buffer. The preparation may be present in the form of, e.g., suspension, solution or emulsion in oily or aqueous medium. The preparation may contain formulating reagent such as suspending agent, stabilizing agent and/or dispersant. In addition, prior to use, the active ingredient may constitute, in the form of powder, a dosage form together with suitable carrier, sterile and apyrogenic water or other solvents. In local application of the invention, foam, gel, ointment, unguent, transdermal patch or cream may be used.

The pharmaceutical composition and method for administration, that are applicable in the invention, include, but are not limited to, the contents described in U.S. Pat. Nos. 5,736,154, 6,197,801 B1, 5,741,511, 5,886,039, 5,941,868, 6,258,374 B1 and 5,686,102.

The dosage for treatment or prevention may be altered according to the severity of disease and the administration route. The administration dosage and frequency are different considering the difference in terms of age, body weight, health status and individual response of patients.

It shall be indicated (the doctor for diagnosis/treatment shall also be aware) that necessary measures must be adopted to stop, interrupt or decrease the dosage of treatment according to the virulence and side reactions. On the contrary, if the clinical response is not obvious (excluding virulence and side reaction), the doctor shall properly change the therapeutic regimen and increase the dosage.

Any suitable administration routes may be used. The dosage form includes tablet, lozenge, fabaceous capsule, dispersant, suspension, solution, capsule, patch and analogs, etc.

In practical application, the compound of the invention, which is alone or in combination with other preparation(s), may be tightly mixed, according to the general pharmaceutical mixing techniques, with pharmaceutical carriers or excipients such as β-cyclodextrin and 2-hydroxypropyl-β-cyclodextrin. According to the requirements of drug administration, common carriers, special carriers for local or parenteral route may be used. For the preparation of parenteral dosage forms, such as compositions for intravenous injection or infusion, similar pharmaceutical media including water, ethylene glycol, oil, buffer, sugar, antiseptic, liposome, etc., which are known to the people skilled in the art, may be used. Examples of these parenteral compositions include, but are not limited to, 5% W/V dextrose, physiological saline or other solutions. The compound of the invention, which is alone or in combination with other preparation(s), may be administrated via a vial of intravenous injection in a total dosage by volume of from 1 ml to 2000 ml. The amount of diluting solution may be altered according to the total dosage of the drug administration.

The invention also provides a kit of implementing the treatment scheme. The kit contains, in one or more vessels, an effective dose of the compound of the invention in a pharmaceutically acceptable form, which is alone or in combination with other preparation(s). The drug is preferably administered together with sterile saline, dextrose solution, buffer solution or other pharmaceutically acceptable sterile liquids. Or, the composition may be lyophilized or dried; and in this case, the kit optionally further contains a pharmaceutically acceptable solution, preferably a sterile solution, in a vessel, thereby reconstituting a composite to form a solution for the purpose of injection. The typical pharmaceutically acceptable solution is physiological saline and dextrose solution.

In another embodiment, the kit of the invention further contains needles or syringes for injecting the composition, which are preferably packaged in sterile form, and/or alcoholic pads packaged. It optionally includes the specification supplied to doctors or patients.

F. Methods of Preparation

All the raw materials used in the invention are synthesized by referring to the method described in the Chinese Patent (Application No: 200310109331.0). The invention is implemented via the following steps:

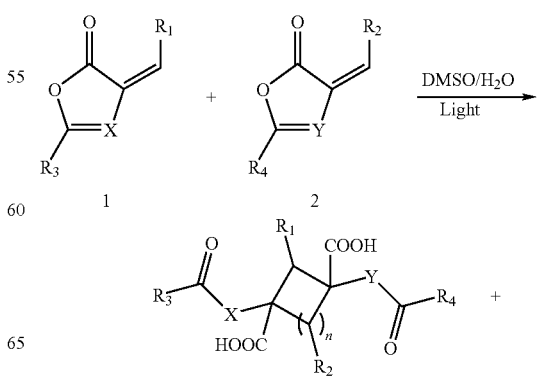

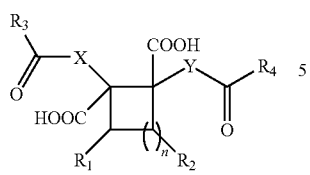

Compound 1 (1 eq) and compound 2 (1 eq) are dissolved in a suitable amount of dichloromethane, water, dichloroethane, DMSO, dioxane or a mixture thereof (to which a catalytic amount of diphenyl ketone is optionally added). The reaction is carried out by controlling the temperature in a range of 0° C.-60° C., under illumination of a 150 W high-pressure mercury lamp or natural light for 1 day to 2 months. During the reaction, the reaction is monitored by detection with HPLC. After the reaction is completed, the reaction solution is lyophilized to remove solvent, and then the remainder is separated with column chromatography to obtain the product.

MODE OF CARRYING OUT THE INVENTION

Experimental Instruments and Reagents

Figure 1:
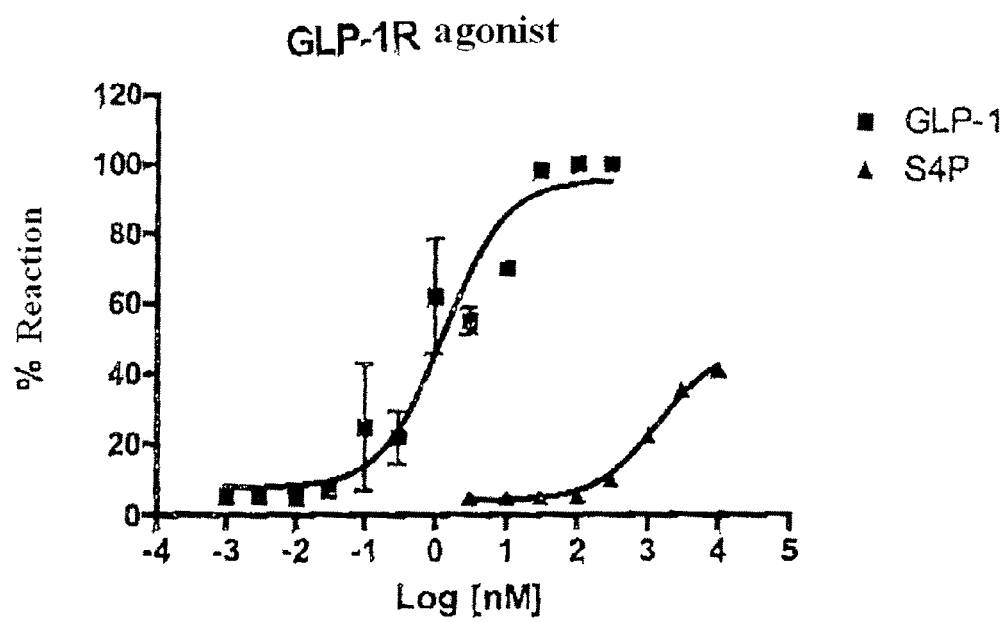
FIG. 1: shows the activating effect of GLP-1 on GLP-1R, as simulated with S4P.

HP 1100 HPLC system, equipped with binary gradient pump, on-line vacuum degassers, automatic sampler, thermostated column compartment and photoelectric diode array detector. The chromatographic column is ZORBAX SB-C18 (2.1×150 mm, 3.5 μm), the mobile phase is acetonitrile/water in a ratio of 65:35, the flow rate is 0.2 ml/min, and the detection wavelength is 254 nm. The melting point is determined by using Type IA6304 melting point instrument; NMR is carried out by using Type Varian Mercury-300 and Varian Mercury plus 400 nuclear magnetic resonance instruments (wherein, the solvent is CDCl$_3$, CD$_3$OD or DMSO-d$_6$); ESI-MS is carried out by using Type AB Mariner mass spectrometer; and EI is carried out by using Type Finnigan MAT95 mass spectrometer. The raw materials used in the synthesis are all commercially available products, unless especially indicated.

The following concrete examples about four-member cyclic compounds make further description on the invention, but not serve to limit the invention.

Example 1

Preparation of Compound S4P and its Derivatives

NMR calibration: δH/C 7.26/77.0 ppm (CDCl$_3$); δH/C 2.50/39.51 ppm (DMSO-d6).

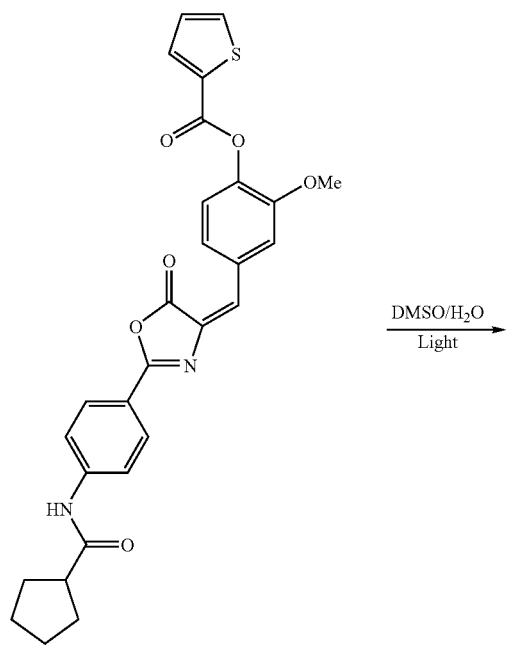

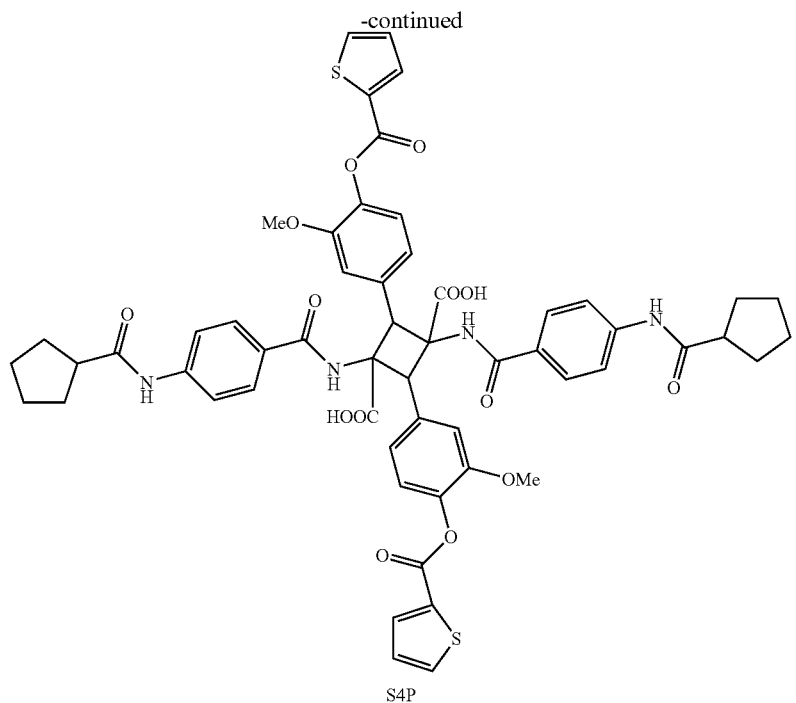

S4P

Compound Wang516 (1 g) was dissolved in a suitable amount of DMSO, and illuminated under a 150 W high-pressure mercury lamp for 3 days. After adding 1 ml of water, the illumination was continued for 7-10 days. During which, the reaction was monitored by detection with HPLC. After the reaction was completed, the reaction solution was lyophilized to remove the solvent, and the remainder was separated with column chromatography to obtain compound S4P as buff powdery solid.

$^1$HNMR (300 MHz, DMSO-d6) 10.053 (2H, br.s), 8.630 (2H, br.s), 8.090 (2H, dd, $J_1$=4.8 Hz, $J_2$=1.2 Hz), 8.029 (2H, dd, $J_1$=3.6 Hz, $J_2$=1.2 Hz), 7.605 (4H, d, J=8.4 Hz), 7.395 (4H, d, J=8.1 Hz), 7.31 (2H, m), 7.280 (2H, br.s), 7.260 (2H, m), 7.206 (2H, br.d, J=8.1 Hz), 4.987 (2H, br.s), 3.244 (6H, s), 2.740 (2H, m), 1.815 (4H, m), 1.703 (4H, m), 1.652 (4H, m), 1.526 (4H, m).

$^{13}$CNMR (75 MHz, DMSO-d6) 174.7, 172.8, 166.8, 159.4, 150.1, 142.1, 137.7, 135.2, 133.6, 131.6, 129.1, 128.7, 128.1, 122.5, 122.1, 118.1, 112.5, 63.2, 54.9, 48.4, 45.3, 30.0, 25.7.

The following product was obtained in the same way:

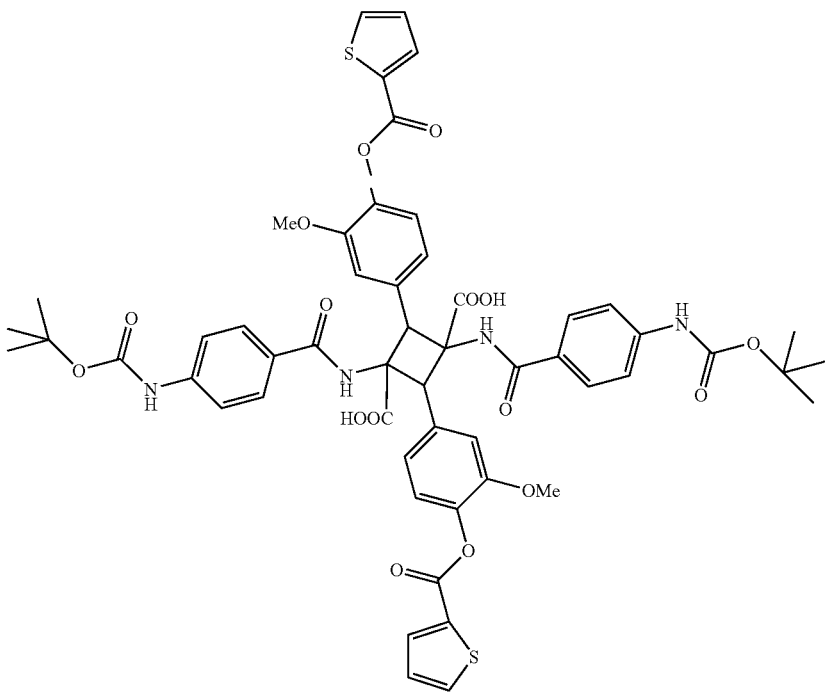

¹HNMR (300 MHz, DMSO-d6) 9.571 (2H, br.s), 8.607 (2H, br.s), 8.078 (2H, d, J=4.8 Hz), 8.035 (2H, d, J=3.3 Hz), 7.464 (4H, d, J=8.4 Hz), 7.363 (4H, d, J=8.1 Hz), 7.31 (2H, m), 7.30 (2H, m), 7.260 (2H, m), 7.216 (2H, br.d, J=8.1 Hz), 4.991 (2H, br.s), 3.270 (6H, s), 1.444 (18H, s).
¹³CNMR (75 MHz, DMSO-d6) 172.8, 166.9, 159.5, 152.6, 150.2, 142.4, 137.8, 135.2, 133.6, 131.7, 128.8, 128.4, 128.2, 122, 117.1, 112, 79.6, 63.2, 54.9, 48, 28.1.
¹HNMR (300 MHz, DMSO-d6) 10.118 (2H, br.s), 8.615 (2H, br.s), 8.095 (2H, dd, J₁=4.8 Hz, J₂=1.2 Hz), 8.027 (2H, dd, J₁=3.9 Hz, J₂=1.5 Hz), 7.569 (4H, d, J=8.4 Hz), 7.365 (4H, d, J=8.7 Hz), 7.318 (2H, dd, J₁=3.9 Hz, J₂=5.1 Hz), 7.280 (2H, m), 7.260 (2H, m), 7.203 (2H, br.d, J=8.1 Hz), 4.981 (2H, br.s), 3.228 (6H, s), 2.015 (6H, s).
Example 2
Preparation of Compound S4P and its Isomers
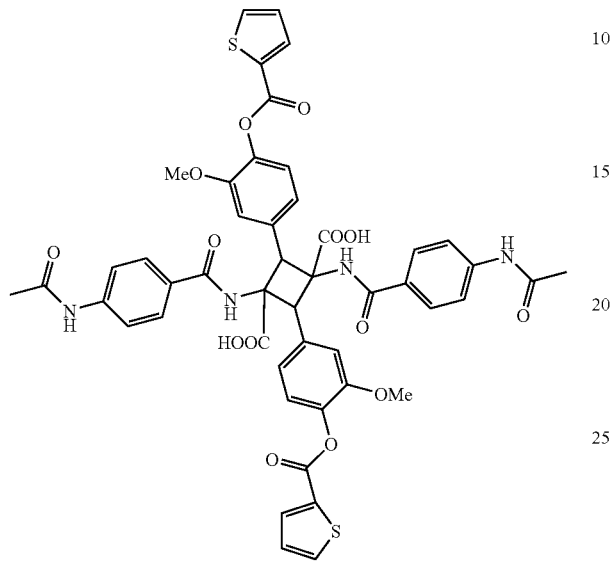
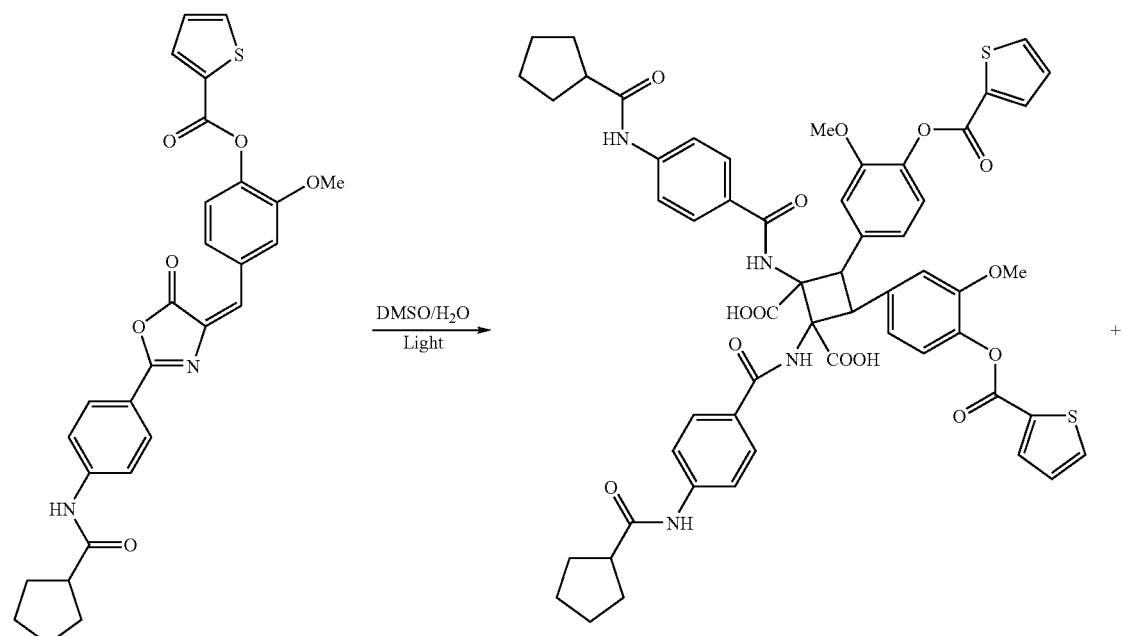

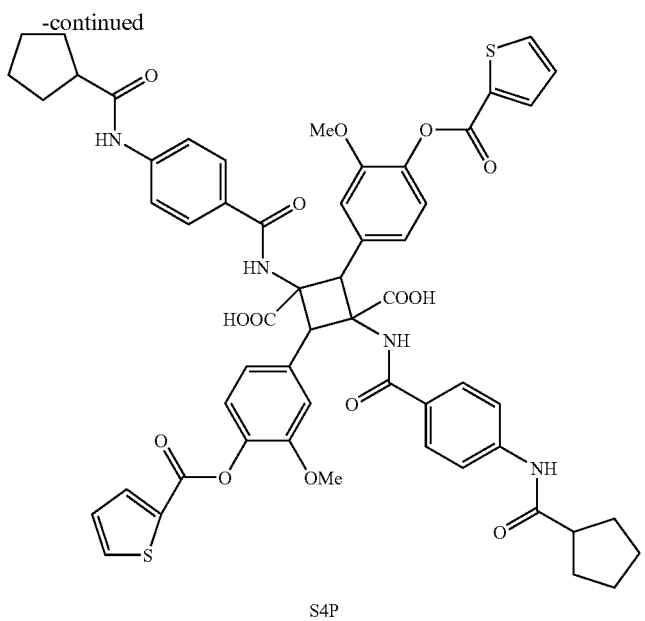

S4P

Compound Wang516 (10 g) was dissolved in a suitable amount of DMSO, and illuminated under natural light at room temperature for 30-90 days. After the reaction was completed, the reaction solution was lyophilized to remove the solvent, and the remainder was separated with HPLC to thereby obtain a very few amount of the regioisomer of compound S4P and the S4P as buff powdery solid.

$^1$HNMR (300 MHz, DMSO-d6) 10.125 (2H, br.s), 8.025 (2H, d, J=4.8 Hz), 7.921 (2H, d, J=2.9 Hz), 7.667 (4H, br.s), 7.251 (2H, m), 7.220 (2H, br.s), 6.983 (2H, d, J=7.7 Hz), 6.908 (2H, d, J=7.7 Hz), 5.269 (2H, br.s), 3.335 (6H, s), 2.779 (2H, m), 1.832 (4H, m), 1.715 (4H, m), 1.677 (4H, m), 1.527 (4H, m).

$^{13}$CNMR (75 MHz, DMSO-d6) 174.8, 174.7, 164.7, 159.5, 149.9, 142.1, 136.5, 135.0, 131.7, 129.3, 128.7, 127.6, 121.8, 120.1, 118.4, 112.0, 64.7, 55.1, 51.8, 45.3, 30.1, 25.7.

The NMR data of S4P were the same as that in Example 1.

Example 3

Preparation of Compound S4P in the Presence of a Catalyst

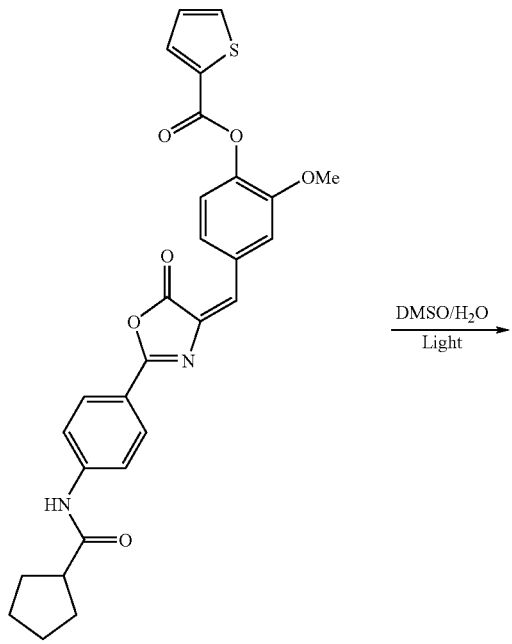

Wang 516

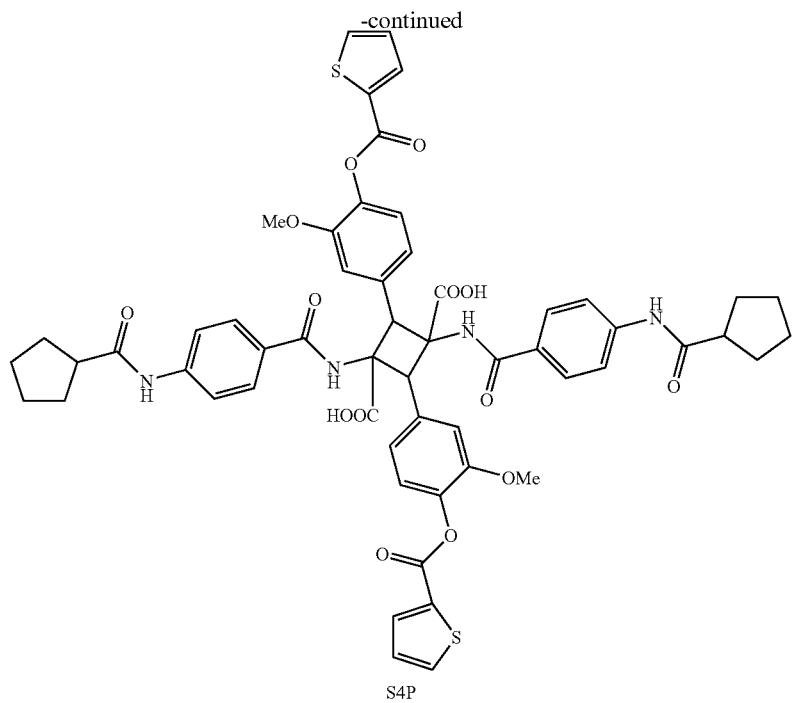

S4P

Compound Wang516 (20 mg) was dissolved in a suitable amount of DMSO, to which 25 mg of diphenyl ketone was added. After illustration under a 150 W high-pressure mercury lamp for 1 day, the reaction solution was lyophilized to remove the solvent, and the remainder was separated with column chromatography to obtain compound S4P as buff powdery solid.

Example 4

Experiments for Testing Biological Activity

1. Testing the Expression of Reporter Gene

GLP-1R is a G-protein coupling receptor. When GLP-1R binds to an agonist, the Ga subunit of G protein is activated to stimulate adenylate cyclase, which leads to the increase in the concentration of intracellular cAMP. Since the promoter region of proinsulin gene has a cAMP response element, cAMP promotes, after binding to this response element, the transcription of the proinsulin gene, thereby stimulating the expression and secretion of insulin (Diabetes, 2000, Vol. 49: 1156-1164). The experimental method employs a human embryonal nephric cell strain (HEK 293) which is stably transfected with the expression vector of GLP-1R gene and the expression vector of luciferase reporter gene under the regulation of cAMP response element, to detect its response to the candidate compound (Cell Biology, 1992, Vol. 89: 8641-8645; Proc. Natl. Acad. Sci. U.S.A. 1987, Vol. 84: 3434-3438). When screening the candidate compounds, the compounds that may induce the expression of luciferase reporter gene are regarded as having the activity of activating GLP-1R.

1.1 Experimental Materials and Instruments

Cell strain: HEK 293/GLP-1R+Luc cell strain, in which GLP-1R and luciferase are stably expressed (self-made by National New Drugs Screening Center);
Fetal bovine serum (GIBCO Co.);
DMEM culture medium (GIBCO Co.);
Steady-Glo™ luciferase analytic system (Promega Co.);
GLP-1 standard (Sigma Co.);
G418 (Invitrogen Co.);
Form a carbon dioxide incubator (Form a Co.);
Victor$^2$ plate-reading machine (Wallac Co.);
Candidate compound: S4P, S3-20-32, S3-11-14, S6-14 and S8.

1.2 Experimental method

HEK 293/GLP-1R+Luc cells were inoculated, in a quantity of 20,000/100 μl/well, into a 96-well culture plate, and cultured at 37° C. overnight with a DMEM culture medium containing 10% fetal bovine serum and 500 μg/ml G418. The GLP-1 standard, and the candidate compounds S4P, S3-20-32, S3-11-14, S6-14 and S8 were respectively diluted to a certain concentration gradient, which were then added, in a quantity of 1/well, into the above 96-well culture plate. The culture was performed under the conditions of 37° C., 5% $CO_2$ for 6 h. Thereafter, the activity of luciferase was detected according to the specification in the kit of Steady-Glo™ luciferase analytic system, and the reading was performed by using a Victor$^2$ plate-reading machine.

1.3 Experimental Results

Figure 2:
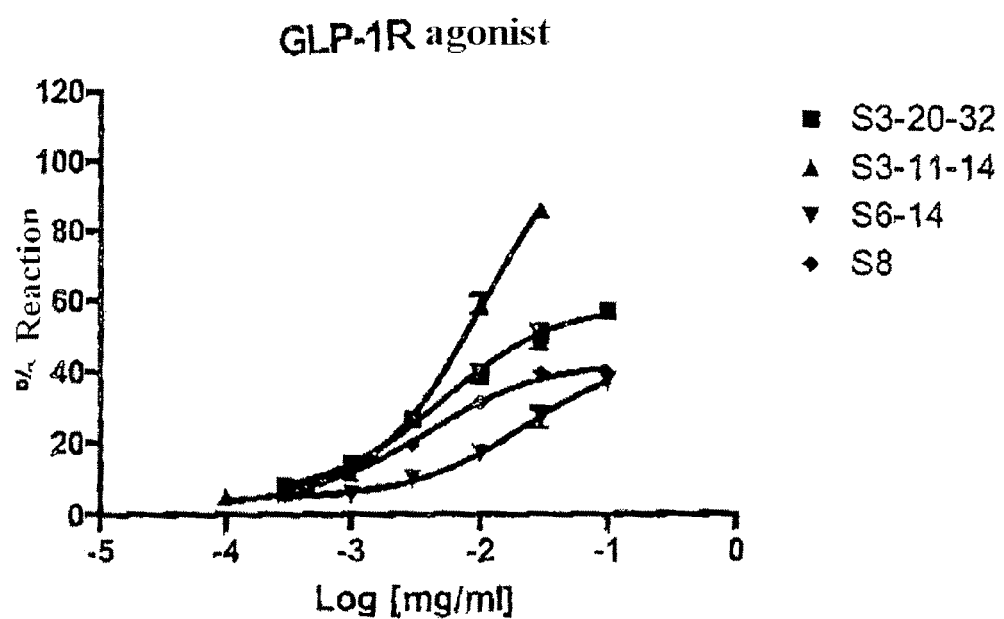
FIG. 2: shows the activating effect of S3-20-32, S3-11-14, S6-14 and S8 on GLP-1R.

The results (Table 1) showed that the compound S3-11-14, in a final concentration of 0.03 mg/ml, had the best relative activating activity (86%) on GLP-1R. In addition, all of the candidate compounds had a dose-dependent profile with respect to their activating activity on GLP-1R (FIG. 1, FIG. 2).

TABLE 1

The results of detecting the expression of the reporter gene
(% reaction, taking the reaction of 30 nM GLP-1 as 100%)

| Final concentration (mg/ml) | S4P | S3-20-32 | S3-11-14 | S6-14 | S8 |
|---|---|---|---|---|---|
| 0.1 | cytotoxic | 57.2351 | non-detected | 37.4351 | 39.6432 |
| 0.03 | cytotoxic | 49.8027 | 86.3973 | 27.1892 | 39.7162 |
| 0.01 | 41.18919 | 39.6432 | 59.2162 | 17.2054 | 31.5135 |
| 0.003 | 35.55405 | 26.7189 | 26.9162 | 9.93243 | 19.6676 |

TABLE 1-continued

The results of detecting the expression of the reporter gene
(% reaction, taking the reaction of 30 nM GLP-1 as 100%)

| Final concentration (mg/ml) | S4P | S3-20-32 | S3-11-14 | S6-14 | S8 |
|---|---|---|---|---|---|
| 0.001 | 22.22703 | 14.0216 | 11.2703 | 5.95405 | 12.073 |
| 0.0003 | 10.19459 | 7.94595 | 5.95405 | 5.25135 | 6.97568 |
| 0.0001 | 5.697297 | non-detected | 5.35135 | non-detected | non-detected |
| 0.00003 | 5.275676 | non-detected | non-detected | non-detected | non-detected |
| 0.00001 | 5.151351 | non-detected | non-detected | non-detected | non-detected |
| 0.000003 | 5.156757 | non-detected | non-detected | non-detected | non-detected |

2. Determination of the Concentration of Intracellular cAMP

Since the concentration of intracellular cAMP can only be indirectly evaluated according to the above method for detecting the activation of reporter gene, it is necessary to determine the influence of active compounds on the concentration of intracellular cAMP by using a cAMP-determining kit, i.e., a functional re-screening.

2.1 Experimental Materials and Instruments cAMP-determining kit (Molecular Devices Co., Catch-Point® Cyclic AMP kit);

Form a carbon dioxide incubator (Form a Co.);

FlexStation™ plate-reading machine (Molecular Devices Co.);

HEK 293/GLP-1R+Luc cell strain, in which GLP-1R and luciferase are stably expressed (self-made by National New Drugs Screening Center);

Candidate compound: S4P, S3-20-32, S3-11-14, S6-14, S8;

cAMP standard (supplied in the kit).

2.2 Experimental Method

HEK 293/GLP-1R+Luc cells were inoculated, in a quantity of 20,000/100 μl/well, into a 96-well culture plate, and cultured at 37° C. overnight. The candidate compounds S4P, S3-20-32, S3-11-14, S6-14 and S8 were respectively diluted to a certain concentration gradient, which were then added, in a quantity of 1/well, into the above 96-well culture plate. The culture was performed under the conditions of 37° C., 5% $CO_2$ for 10 min. Thereafter, the concentration of intracellular cAMP was determined according to the specification in CatchPoint® Cyclic AMP kit.

2.3 Experimental Results

Figure 3:
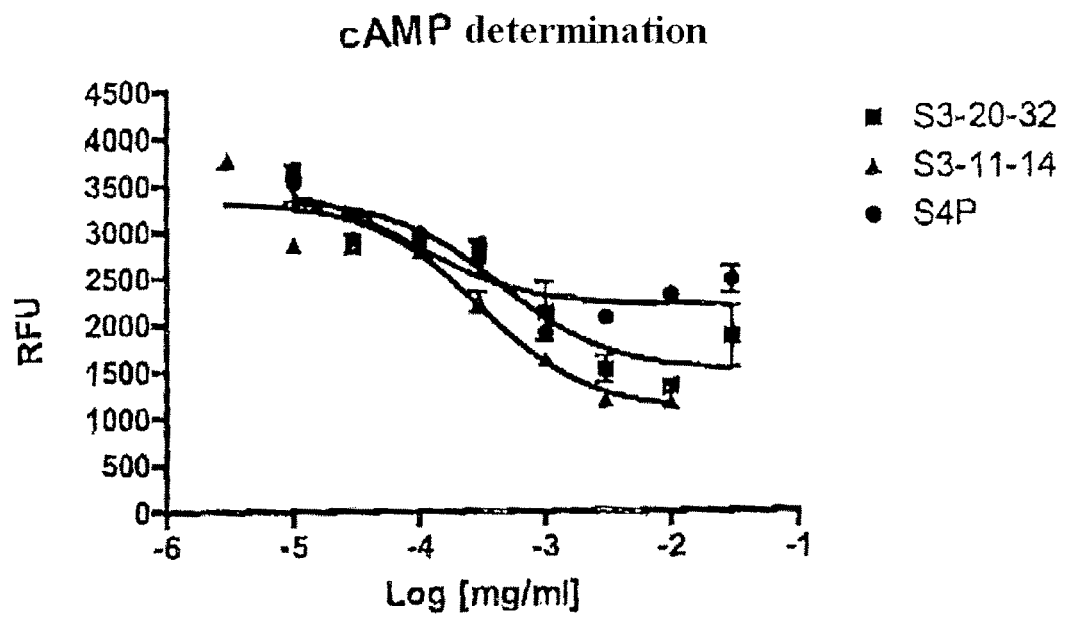
FIG. 3: shows the influences of S4P, S3-20-32 and S3-11-14 on the concentration of intracellular cAMP.
Figure 4:
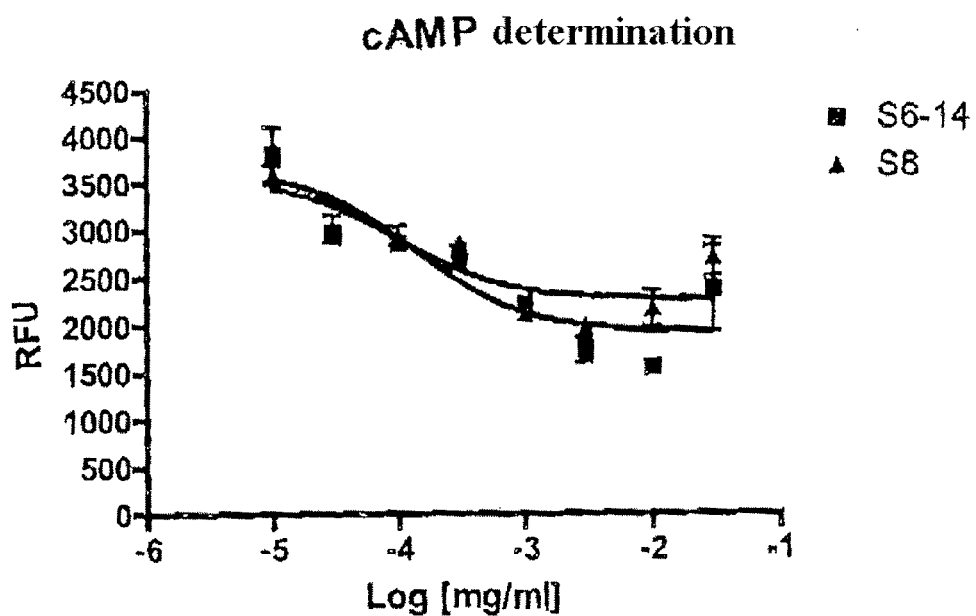
FIG. 4: shows the influences of S8 and S6-14 on the concentration of intracellular cAMP.
Figure 5:
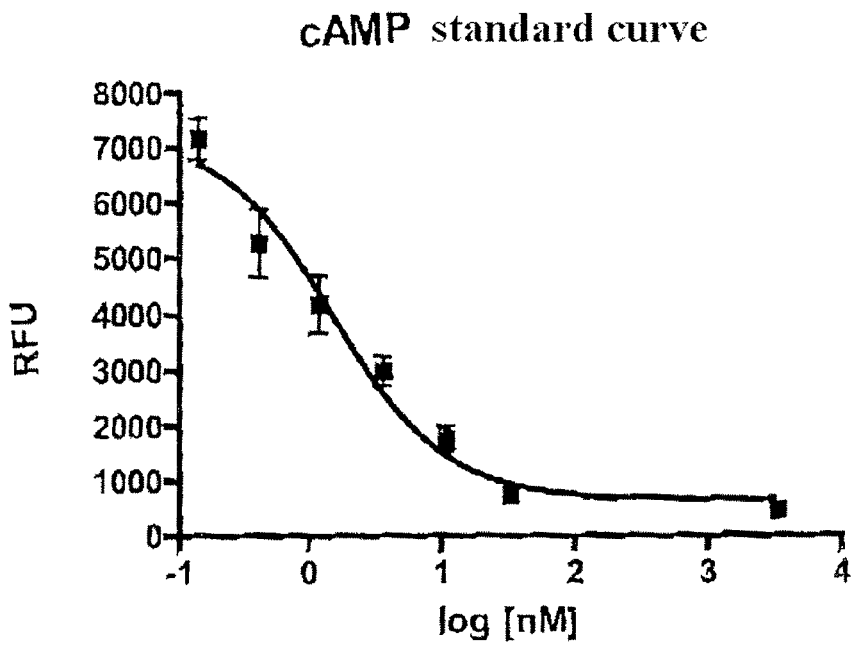
FIG. 5: shows the dosage-response profile of exogenous cAMP.

The results for determining the concentration of intracellular cAMP were shown in Table 2. The lower the reading was, the higher the concentration of intracellular cAMP was. With increasing of the concentration of the candidate compound, the concentration of cAMP that was produced under its stimulation showed an exponential increase (FIG. 3, FIG. 4). It was demonstrated that all of the candidate compounds exhibited the activity as GLP-1R agonists. FIG. 5 shows the standard curve of cAMP.

TABLE 2

The results of determining the concentration of the intracellular cAMP
(unit: RFU, relative fluoresence intensity)

| Final concentration (mg/ml) | S4P | S3-20-32 | S3-11-14 | S6-14 | S8 |
|---|---|---|---|---|---|
| 0.03 | 2480.017 | 1864.021 | non-determined | 2377.238 | 2710.627 |
| 0.01 | 2310.616 | 1336.377 | 1173.811 | 1550.334 | 2172.538 |
| 0.003 | 2072.988 | 1518.5 | 1198.391 | 1736.374 | 1983.304 |
| 0.001 | 1910.855 | 2133.249 | 1632.893 | 2223.694 | 2116.336 |
| 0.0003 | 2708.597 | 2785.435 | 2241.339 | 2709.84 | 2866.183 |
| 0.0001 | 2985.794 | 2921.118 | 2799.376 | 2864.305 | 2939.641 |
| 0.00003 | 2924.461 | 2875.325 | 2969.218 | 2976.46 | 3016.52 |
| 0.00001 | 3536.618 | 3655.632 | 2866.55 | 3818.542 | 3598.147 |
| 0.000003 | non-determined | non-determined | 3783.91 | non-determined | non-determined |

3. Antagonistic Experiment with $Exendin_{9-39}$

In order to corroborate that the active compounds had receptor specificity with respect to their activating effects on reporter gene and intracellular cAMP, $Exendin_{9-39}$ (Eur. J. Pharmacol, 1994, 269: 183-191; Metabolism 2004, 53:252-259.), a specific antagonist of GLP-1R, was used to validate whether it could antagonize the agonistic activity of the above representative compounds to GLP-1R.

3.1 Experimental Materials and Instruments

Cell strain: HEK 293/GLP-1R+Luc cell strain, in which GLP-1R and luciferase are stably expressed (self-made by National New Drugs Screening Center);

Fetal bovine serum (GIBCO Co.);

DMEM culture medium (GIBCO Co.);

Exendin 9-39 (AnaSpec Co.);

Steady-Glo™ luciferase analytic system (Promega Co.);

G418 (Invitrogen Co.);

Forma carbon dioxide incubator (Forma Co.);

$Victor^2$ plate-reading machine (Wallac Co.);

Candidate compound: S4P.

3.2 Experimental Method

HEK 293/GLP-1R+Luc cells were inoculated, in a quantity of 20,000/100 μl/well, into a 96-well culture plate, and cultured at 37° C. overnight with a DMEM culture medium containing 10% fetal bovine serum and 500 μg/ml G418. $Exendin_{9-39}$ was diluted to a certain concentration gradient, which was then added, in a quantity of 1 μl/well, into the above 96-well culture plate. The culture was performed under the conditions of 37° C., 5% $CO_2$ for 6 h. Thereafter, the activity of luciferase was detected according to the specification in the kit of Steady-Glo™ luciferase analytic system, and the reading was performed by using a $Victor^2$ plate-reading machine.

Figure 6:
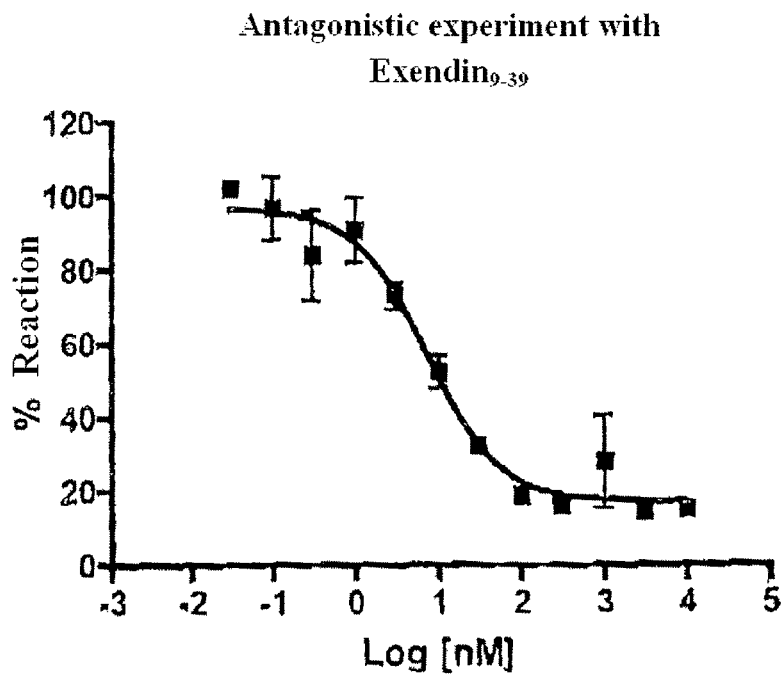
FIG. 6: shows the inhibitory effect of the GLP-1R antagonist Exendin$_{9-39}$ on the biological activity of S4P.

3.3 Experimental Results $Exendin_{9-39}$ could inhibit, in a dose-dependent manner, the expression of reporter gene induced by S4P (see Table 3, FIG. 6), which demonstrated that the biological activity of S4P is mediated by GLP-1R.

TABLE 3

The antagonistic effect of $Exendin_{9-39}$ on S4P (% reaction,
taking the reaction of 3 μM S4P as 100%)

| $Exendin_{9-39}$ final concentration (nM) | S4P |
|---|---|
| 10000 | 15.22131 |
| 3000 | 14.56557 |

TABLE 3-continued

The antagonistic effect of Exendin$_{9-39}$ on S4P (% reaction, taking the reaction of 3 µM S4P as 100%)

| Exendin$_{9-39}$ final concentration (nM) | S4P |
|---|---|
| 1000 | 27.96721 |
| 300 | 15.96721 |
| 100 | 18.77049 |
| 30 | 32.32787 |
| 10 | 52.47541 |
| 3 | 72.83607 |
| 1 | 90.77869 |
| 0.3 | 83.84426 |
| 0.1 | 96.63934 |
| 0.03 | 101.8115 |

What is claimed:

1. A substituted cyclic compound of the following general formula I or II or pharmaceutically acceptable salts thereof:

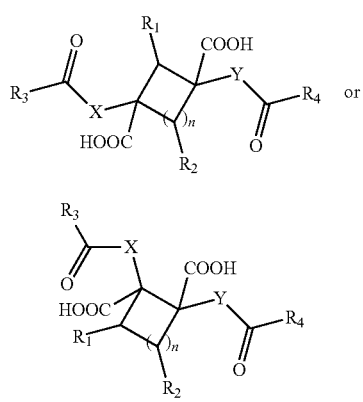

wherein:
n is 0 or 1;
X and Y are NH;
wherein, $R_1$ and $R_2$ independently are one of the substituents selected from the group consisting of: aryl; 2-, 3- or 4-pyridyl; aryl substituted with one, two or three groups selected from $C_1$-$C_4$ alkyl, alkoxy, mercapto, methylthio, ethylthio, —O—$C_1$-$C_6$ alkanoyl substituted with one, two or three groups selected from halogen, $C_1$-$C_6$ alkoxy, or hydroxyl, and thienyl-2-carboxylate; and 2-, 3- or 4-pyridyl substituted with one, two or three groups selected from $C_1$-$C_4$ alkyl, alkoxy, mercapto, methylthio, ethylthio, —O—$C_1$-$C_6$ alkanoyl substituted with one, two or three groups selected from halogen, $C_1$-$C_6$ alkoxy, or hydroxyl, and thienyl-2-carboxylate; and $R_3$ and $R_4$ independently are one of the substituents selected from the group consisting of: aryl; 2-, 3- or 4-pyridyl; aryl substituted with one, two or three groups selected from $C_1$-$C_4$ alkyl, alkoxy, mercapto, methylthio, ethylthio, —NH—$C_1$-$C_6$ alkanoyl substituted with one, two or three groups selected from halogen, $C_1$-$C_6$ alkoxy, or hydroxyl, —NH—$C_3$-$C_6$ cycloalkanoyl, and —NH—$C_3$-$C_6$ cycloalkanoyl substituted with one, two or three groups selected from halogen, $C_1$-$C_6$ alkoxy, and hydroxyl; and 2-, 3- or 4-pyridyl substituted with one, two or three groups selected from $C_1$-$C_4$ alkyl, alkoxy, mercapto, methylthio, ethylthio, and —NH—$C_1$-$C_6$ alkanoyl substituted with one, two or three groups selected from halogen, $C_1$-$C_6$ alkoxy, or hydroxyl.

2. The substituted cyclic compound or pharmaceutically acceptable salts thereof according to claim 1, wherein:
$R_1$ and $R_2$ independently are

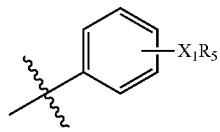

wherein, $R_5$ is one of the substituents selected from the group consisting of: $C_1$-$C_6$ alkyl; $C_1$-$C_6$ alkanoyl substituted with one, two or three groups selected from halogen, $C_1$-$C_6$ alkoxy, and hydroxyl; and thenoyl;
$X_1$ is O;
$R_3$ and $R_4$ independently are

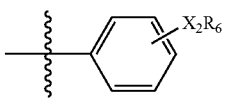

wherein, $R_6$ is one of the substituents selected from the group consisting of: $C_1$-$C_6$ alkyl; $C_1$-$C_6$ alkanoyl substituted with one, two or three groups selected from halogen, $C_1$-$C_6$ alkoxy, and hydroxyl; $C_2$-$C_6$ enoyl; $C_2$-$C_6$ alkynoyl; $C_3$-$C_6$ cycloalkanoyl; and $C_3$-$C_6$ cycloalkanoyl substituted with one, two or three groups selected from halogen, $C_1$-$C_6$ alkoxy, and hydroxyl;
$X_2$ is NH;
Or
$R_1$ and $R_2$ independently are

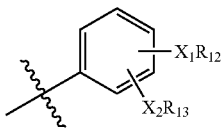

wherein, $R_{12}$ and $R_{13}$ independently are one of the substituents selected from the group consisting of: $C_1$-$C_6$ alkyl; halogen, $C_1$-$C_6$ alkanoyl substituted with one, two or three groups selected from halogen, $C_1$-$C_6$ alkoxy, and hydroxyl; and thenyl;
$X_1$ is O;
$X_2$ is O;
$R_3$ and $R_4$ independently are

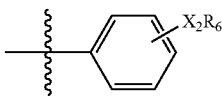

wherein, $R_6$ is one of the substituents selected from the group consisting of: $C_1$-$C_6$ alkyl; $C_1$-$C_6$ alkanoyl substituted with one, two or three groups selected from halogen, $C_1$-$C_6$ alkoxy, and hydroxyl; $C_2$-$C_6$ alkenoyl; $C_2$-$C_6$ alkynoyl; $C_3$-$C_6$ cycloalkanoyl; $C_3$-$C_6$ cycloalkanoyl substituted with one, two or three groups selected from halogen, $C_1$-$C_6$ alkoxy, and hydroxyl;
$X_2$ is NH.

3. A pharmaceutical composition comprising the substituted cyclic compound or therapeutically acceptable salts thereof according to claim 1 or 2 as active ingredient.

4. The pharmaceutical composition according to claim 3, which further comprises pharmaceutically acceptable carriers and excipients.

5. A combined preparation, comprising the compound according to claim 1 or pharmaceutically acceptable salts thereof and other drugs for treating diabetes.

6. The combined preparation according to claim 5, wherein the other drugs are rosiglitazone and pioglitazone.

7. A kit, comprising the compound according to claim 1 or pharmaceutically acceptable salts thereof.

8. A kit, comprising the combined preparation according to claim 5.

* * * * *